United States Patent [19]

Wallner et al.

[11] Patent Number: 4,956,281
[45] Date of Patent: Sep. 11, 1990

[54] DNA SEQUENCES, RECOMBINANT DNA MOLECULES AND PROCESSES FOR PRODUCING LYMPHOCYTE FUNCTION ASSOCIATED ANTIGEN-3

[75] Inventors: Barbara P. Wallner, Cambridge; Timothy A. Springer, Newton; Catherine Hession, South Weymouth; Richard Tizard, Cambridge; Robert Mattaliano, Newton; Michael L. Dustin, Boston, all of Mass.

[73] Assignees: Biogen, Inc., Cambridge; Dana Farber Cancer Institute, Inc., Boston, both of Mass.

[21] Appl. No.: 57,615

[22] Filed: Jun. 3, 1987

[51] Int. Cl.$^5$ .................... C12P 21/00; C12N 15/00; C12N 1/20

[52] U.S. Cl. ............................. 435/69.3; 435/252.31; 435/252.33; 435/252.34; 435/252.35; 435/254; 435/240.2; 435/240.4; 435/172.3; 435/320; 536/27; 935/1; 935/11; 935/12; 935/27; 935/32; 935/70; 935/71; 935/72

[58] Field of Search ................. 435/68, 70, 91, 172.3, 435/243, 253, 254, 240.2, 320; 935/11, 12, 15, 27, 32, 70, 71

[56] References Cited

U.S. PATENT DOCUMENTS

4,728,927  1/1988  Taniguchi et al. ................ 340/146.2

OTHER PUBLICATIONS

Sewall et al., Proc. Natl. Acad. Sci. vol. 83 1986 pp. 8718-8722.
David M. Kranz et al., "Immunoprecipitation of Cell Surface Structures of Cloned Cytotoxic T Lymphocytes by Clone-Specific Antisera," Proc. Natl. Acad. Sci. U.S.A., vol. 81, pp. 573-77 (1984).
M. William Makgoba et al., "Human T Cell Rosetting is Mediated by LFA-3 on Autologous Erythrocytes," Journ. Immunol., vol. 138, pp. 3587-89 (1987).
Benton et al., "Screening the Recombinant Clones by Hybridization to Single Plaques in situ", Science, 196, 180-182 (1977).
Cate, et al., "Isolation of the Bovine and Human Genes for Mullerian Inhibiting Substance and Expression of the Human Gene in Animal Cells", Cell, 45, 685-698 (1986).
Church, et al., "Genomic Sequencing", Proc. Natl. Acad. Sci. U.S.A., 81, 1991-1995 (1984).
Dustin, et al., "Purified Lymphocyte Function-Associate Antigen 3 Binds to CD2 and Mediates T Lymphocyte Adhesion", J. Exp. Med., 165, 677-92 (1987).
Grosveld, et al., "The Construction of Cosmid Libraries Which Can Be Used to Transform Eukaryotic Cells", Nucl. Acids. Res., 10, 6715-6732 (1982).
Gubler, et al., "A Simple and Very Efficient Method for Generating cDNA Libraries", Gene, 25, 263-269 (1983).
Hawkes, et al., "A Dot-Immunobinding Assay for Monoclonal and Other Antibodies", Anal. Biochem., 119, 142-147 (1982).
Hewick, et al., "A Gas-Liquid Solid Phase Peptide and Protein Sequentor", J. Biol. Chem., 256, 7990-7997 (1981).
Maniatis, et al., "Extraction, Purification, and Analysis of mRNA from Eukaryotic Cells", Molecular Cloning, 187-209 (1982).

(List continued on next page.)

Primary Examiner—Robin L. Teskin
Assistant Examiner—Beth A. Burrous
Attorney, Agent, or Firm—James F. Haley, Jr.; Leon R. Yankwich; Teresa L. Solomon

[57] ABSTRACT

Polypeptides that bind to CD2, the receptor on the surface of T-lymphocytes. Most preferably, the polypeptides bind to CD2 on the surface of T-lymphocytes and inhibit adhesion between T-lymphocytes and target cells. DNA sequences that code on expression in appropriate unicellular hosts for those polypeptides. Methods of making and using those polypeptides in therapy and diagnosis.

10 Claims, 5 Drawing Sheets

OTHER PUBLICATIONS

March, et al., "A Simplified Method for Cyanogen Bromide Activation of Agarose for Affinity Chromatography", *Anal. Biochem.*, 60, 149–152 (1974).

Maxam, et al., "A New Method for Sequencing DNA", *Proc. Natl. Acad. Sci.*, 74, 560–564 (1977).

Maxam et al., "Sequencing End–Labeled DNA with Base-Specific Chemical Cleavages", *Meth. Enzymology*, 65, 499–560 (1980).

Mulligan et al., "Selection for Animal Cells that Express the *Escherichia Coli* Gene Coding for Xanthine-Guanine Phophoribosyltransferase", Proc. Natl. Acad. Sci. U.S.A., 78, (1981).

Okayama, et al., "High-Efficiency Cloning of Full-Length cDNA", *Mol. Cell. Biol.*, 2, 161–170 (1982).

Pepinsky, et al., "Purification and Partial Sequence Analysis of a 37-kDA Protein that Inhibits Phospholipase $A_2$ Activity from Rat Peritoneal Exudates", *J. Bio. Chem.*, 262, 4239–4246 (1986).

Sanchez-Madrid, et al., "Three Distinct Antigens Associated with Human T-Lymphocytemediated Cytoloysis: LFA-2, and LFA-3", *Proc. Natl. Acad. Sci. U.S.A.*, 79, 7489–93 (1982).

Southern, E. M. "Detection of Specific Sequences Among DNA Fragments Separated by Gel Electrophoresis", *J. Mol. Biol.*, 98, 503–517 (1975).

Springer, et al., "The Lymphocyte Function-Associated LFA-1, CD2, and LFA-3 Molecules: Cell Adhesion Receptors of the Immune System", *Ann. Rev. Immuno.*, 5, 223–52 (1987).

Wallner, et al., "Cloning and Expression of Human Lipocortin, a Phospholipase A2 Inhibitor with Potential Anti-Inflammatory Activity", *Nature*, 320, 77–81 (1986).

Wong et al., "Identification of a Partial cDNA Clone for the Human Receptor for Completement Fragments C3b/C4b", *Proc. Natl. Acad. Sci. U.S.A.*, 82, 7711–775 (1985).

FIG. 1

```
NH2 Terminus  :  FSQQIYGVVYGXVTFHVPSNVP
LFA-3            LKEVLWKKQKDKVAEL

T72-73        :  DKVAELENSEF

T91           :  VYLDTVSGSLTIYNLTS

T105          :  FFLYVLESLPSPTLTCAL

T68           :  GLIMYS
```

FIG. 4

```
                                      |------ Cloning Sites ------|
         N                B   E        H    S
         o              a m  c        i    a    N
         t              m S  o        n    c    N
         1              H a  R        D    1    3
         |              |c|  |        |    |    |
5'-atgaccatgattacgaattGCGGCCGGATTGGGATGTGAGGATCCCGGAATTCGAGCTCAAGCTTTGAGATTGGTGGTTGGACCGGCGGCCGCTagcttggcactggc-3'
                     5'-CGGATTGGGATGTGAGGATC-3' NN-C     5'-CTTTGAGATTGGTGGTTGGA-3' NN-D
                     3'-GCCTAACCCTACACTCCTAG-5' NN-A     3'-GAAACTCTAACCACCAACCT-5' NN-B
3'-tactggtactaatgcttaaCGCCGGCCTAACCCTACACTCCTAGGGCCCTTAAGCTCGAGTTCGAAACTCTAACCACCAACCTGGCCGCCGGAtcgaaccgtgaccg-5'
         |              |   |  |        |    |    |
         N              S   a  m        a    S    N
         o              a   c  c        c    a    N
         t              c   |  o        |    c    -
         1              2      R        D    2    B

|---- pUC ---->
|---- pUC ---|
```

FIG. 2

Oligonucleotide Probe Pool LF1:
20mer, 32fold degenerate

Corresponds to amino acid sequence:

```
           trp  lys  lys  gln  lys  asp  lys
5'         TGG  AAA  AAA  CAG  AAA  GAC  AAA
                 G    G    A    G    T    G
```

Probe Sequence:

```
3'         ACC  TTT  TTT  GTC  TTT  CTG  TT
                 C    C    T    C    A
```

Oligonucleotide Probe Pool LF2-5:
20mer 384fold degenerate. Synthesized in four subpools of 96fold degeneracy.

Correspond to amino acid sequence:

```
           gln  gln  ile  tyr  gly  val  val
5'         CAG  CAG  ATC  TAC  GGN  GTN  GTN
            A    A    T    T
                      A
```

Probe Sequence:

```
         3' GTC GTC TAG ATG CCN CAN CA
                T   T   A   A
                        T
LF2:     3' GTC GTC TAG ATG CCA CAN CA
                T   T   A   A
                        T
LF3:     3' GTC GTC TAG ATG CCT CAN CA
                T   T   A   A
                        T
LF4:     3' GTC GTC TAG ATG CCG CAN CA
                T   T   A   A
                        T
LF5:     3' GTC GTC TAG ATG CCC CAN CA
                T   T   A   A
                        T
```

FIG. 3A

DNA Sequence and Amino Acid Sequence of Human LFA3

```
    GAATTCCCGACGAGCCATGGTTGCTGGGAGCGACGCGGGGGACGCGGGGTCCCTGGGGTCCTCAGCTGTCTCGCCTGCTGCTTGGTTCATCAGCTGT
1   -------+---------+---------+---------+---------+---------+---------+---------+---------+---------+  100
    CTTAAGGGCTGCTCGGTACCAACGACCCTCGCTGCCGCCCCCAGGGACCCCAGGAGTCGACGGACGACGTGACGAACCAAAGTAGTCGACA
                                                 -28  M  V  A  G  S  D  A  G  R  A  L  G  V  L  S  V  V  C  L  L  H  C  F  G  F  I  S  C   -1

TTTCCCAACAAATATATGGTGTTGTGATGTATGGAATGTAACTTTCCATGTACCAAGCAATGTGCCTTTAAAAGAGTCCTATGGAAAAACAAAGGATA
101 -------+---------+---------+---------+---------+---------+---------+---------+---------+---------+  200
    AAAGGGTGTTTATATACCACACAACACTATACCCTTACATTGAAAGGTACATGGTTCGTTACACGGAAATTTTCTCCAGGATACCTTTTGTTTCCTAT
      F  S  Q  Q  I  Y  G  V  V  Y  G  N  V  T  F  H  V  P  S  N  V  P  L  K  E  V  L  W  K  K  Q  K  D  K  34
    1                                                                                                   34

AAGTTGCAGAACTGGAAATTCTGAATTCAGAGCTTTCTCATCTTTAAAAATAGGGTTTATTTAGACACTGTGTCAGGTAGCCTCACTATCTACAACTT
201 -------+---------+---------+---------+---------+---------+---------+---------+---------+---------+  300
    TTCAACGTCTTGACCTTTAAGACTTAAGTCTCGAAAGAGTAGAAATTTTATCCCAAATAAATCGTGACACAGTCCATCGGAGTGATAGATGTTGAA
      V  A  E  L  E  N  S  E  F  R  A  F  S  S  F  K  N  R  V  V  L  D  T  V  S  G  S  L  T  I  V  N  L
    35                                                                                                  67

AACATCATCAGATGAAGATGAGTAGTCATGAAATGGAATCGCCAAATATTACTGATACCATGAAGTTCTTTCTTATGTGCTTGAGTCTCTTCCATCTCCCACA
301 -------+---------+---------+---------+---------+---------+---------+---------+---------+---------+  400
    TTGTAGTAGTCTACTTCTACTCATGATGAGTACTTTACCTTAGCGGTTATAATGACTATGGTACTTCAAGAAGAAATACACGAACTCAGAGAAGGTAGAGGGTGT
      T  S  S  D  E  D  E  V  E  M  E  S  P  N  I  T  D  T  M  K  F  F  L  V  L  E  S  L  P  S  P  T
    68                                                                                                  100

CTAACTTGTGCATTGACTAATGGAAGCATTGAAGTCCAATGCCATGATACCAGAGCCATTACAACAGCCATCGAGGACTTATAATGTACTCATGGATTGTC
401 -------+---------+---------+---------+---------+---------+---------+---------+---------+---------+  500
    GATTGAACACGTAACTGATTACCTTCGTAACTTCGTAACTTCAGTTACTTGCGTAATGTTGTCGGTAGCCTCCTGAATATTACATGAGTACCCTAACAG
```

FIG. 3B

```
101  L  T  C  A  L  T  N  G  S  I  E  V  Q  C  M  I  P  E  H  V  N  S  H  R  G  L  I  M  Y  S  W  D  C  P   134
     CTATGGAGCAATGTAAACGTAACTCAACCAGTATATATTTAAGATGGAAAATGATCTTCCACAAAAATACAGTGTACTCTTAGCAATCCATTATTTAA      600
501  -----+---------+---------+---------+---------+---------+---------+---------+---------+---------+
     GATACCTCGTTACATTGCATTGAGTTGGTCATATATAAATTCTACCTTTATGTCACATGAGAATCGTTAGGTAATAAATT

135  M  E  Q  C  K  R  N  S  T  S  I  Y  F  K  M  E  N  D  L  P  Q  K  I  Q  C  T  L  S  N  P  L  F  N   167
     TACAACATCATCAATCATTTGACAACCTGTATCCCAAGCAGGCGTCATTCAAGACACAGATGCACTTATACCCATTAGCAGTAATTACAACA         700
601  -----+---------+---------+---------+---------+---------+---------+---------+---------+---------+
     ATGTGTAGTAGTAAATTTGATTTTTCGTCGCCAGTAAGTTCTGTGTCTATACGTAAGTTGGTATGGTATGGTAATCGTCATTAATGTGT

168  T  T  S  S  I  L  T  T  C  I  P  S  S  G  H  S  R  H  R  Y  A  L  I  P  I  P  L  A  V  I  T  T    200
     TGTATTGTGCTGTATATGAATGTATTCTGAAATGTGACAGAAACCAGACAGAAACTCCATTGATTGGTAACAGAAGATGAAGACAACAGCATAA       800
701  -----+---------+---------+---------+---------+---------+---------+---------+---------+---------+
     ACATAACACGACATATACTTACCATAAGACTTTACACGTCTTTGGTCTGCTTGGTTAACTAACCATTGTCTTACTTCTGTTCTGTATT

201  C  I  V  L  V  M  N  G  I  L  K  C  D  R  K  P  D  R  T  N  S  N   222
     CTAAATTATTTTAAAACTAAAAAGCCATCTGATTTCTCATTTGAGTATTACAATTTTTGAACAACGTGTTGGAAATGTAACTTGAAGCAGCTGCTTTAAG  900
801  -----+---------+---------+---------+---------+---------+---------+---------+---------+---------+
     GATTTAATAAATTTTGATTTTTCGGTAGACTAAAGAGTAAACTCATATAATGTTAAAACTTCATTGAACTTCGTCGACGAAATTC

AAGAAATACCCACTAACAAGAACAAGCATTAGTTTTGGCTGTCATCAACTTATTATATGACTAGGTGCTTGCTTTTTTTGTCAGTAAATTGTTTTACT   1000
901  -----+---------+---------+---------+---------+---------+---------+---------+---------+---------+
     TTCTTTATGGGTGATTGTTTCTTGTTCGTAATCAACAAAACCGACAGTAGTTGAATAATATACTGATCCACGAACGAAAAAACAGTCATTTAACAAAATGA

GATGAGTGTAGATACTTTTGTAAATAAAATGTAAAATATGTACACAAGGG   1047
1001 -----+---------+---------+---------+---------+
     CTACTACACTCTATGAAAACATTTATTATTTACATTTATACATGTGTTCCC
```

FIG. 5

LF-10 : cgtcgctcccagcaaccatggctcgtcggg
LF-11 : catggaaagttacattcccatacacaacacc
NN-A  : gatcctcacatcccaatccg
NN-B  : tccaaccaccatctcaaag
NN-C  : cggattgggatgtgaggatc
NN-D  : ctttgagattggtgtggtttgga

DNA SEQUENCES, RECOMBINANT DNA MOLECULES AND PROCESSES FOR PRODUCING LYMPHOCYTE FUNCTION ASSOCIATED ANTIGEN-3

This invention relates to DNA sequences, recombinant DNA molecules and processes for producing Lymphocyte Function Associated Antigen-3 (LFA-3). More particularly, the invention relates to DNA sequences that are characterized in that they code on expression in an appropriate unicellular host for LFA-3 or derivatives thereof that bind to CD2, the receptor on the surface of T-lymphocytes. More preferably, the LFA-3 of this invention and its derivatives bind to CD2 on the surface of T-lymphocytes. Most preferably, they also inhibit adhesion between T-lymphocytes and target cells. In accordance with this invention, unicellular hosts transformed with these DNA sequences and recombinant DNA molecules containing them may also be employed to produce LFA-3 essentially free of other proteins of human origin. This novel antigen may then be used in the therapeutic and diagnostic compositions and methods of this invention.

BACKGROUND OF THE INVENTION

T-lymphocytes play a major role in the immune response by interacting with target and antigen presenting cells. For example, the T-lymphocyte mediated killing of target cells is a multi-step process involving adhesion of a cytolytic T-lymphocyte to a target cell. And, helper T-lymphocytes initiate the immune response by adhesion to antigen-presenting cells.

These interactions of T-lymphocytes with target and antigen-presenting cells are highly specific and depend on the recognition of an antigen on the target or antigen-presenting cell by one of the many specific antigen receptors on the surface of the T-lymphocyte.

The receptor-antigen interaction of T-lymphocytes and other cells is also facilitated by various T-lymphocyte surface proteins, e.g., the antigen receptor complex CD3(T3) and accessory molecules CD4, LFA-1, CD8, and CD2. It is also dependent on accessory molecules, such as LFA-3, ICAM-1 and MHC that are expressed on the surface of the target or antigen-presenting cells. In fact, it is hypothesized that the accessory molecules on the T-lymphocytes and on the target or antigen-presenting cells interact with each other to mediate intercellular adhesion. Accordingly, these accessory molecules are thought to enhance the efficiency of lymphocyte-antigen-presenting cell and lymphocyte-target cell interactions and to be important in leukocyte-endothelial cell interactions and lymphocyte recirculation.

For example, recent studies have suggested that there is a specific interaction between CD2 (a T-lymphocyte accessory molecule) and LFA-3 (a target cell accessory molecule) that mediates T-lymphocyte adhesion to the target cell. This adhesion is essential to the initiation of the T-lymphocyte functional response (M. L. Dustin et al., "Purified Lymphocyte Function-Associated Antigen-3 Binds To CD2 And Mediates T Lymphocyte Adhesion, *J. Exp. Med.*, 165, pp. 677-92 (1987); Springer et al., *Ann. Rev. Immunol.* (1987) (in press)). And, monoclonal antibodies to either LFA-3 or CD2 have been shown to inhibit a spectrum of cytolytic T lymphocyte and helper T lymphocyte dependent responses (F. Sanchez-Madrid et al., "Three Distinct Antigens Associated With Human T-Lymphocyte-Mediated Cytolysis: LFA-1, LFA-2, And LFA-3", *Proc. Natl. Acad. Sci. USA*, 79, pp. 7489-93 (1982)).

LFA-3 is found on antigen-presenting cells, and target cells, specifically on monocytes, granulocytes, CTL's, B-lymphoblastoid cells, smooth muscle cells, vascular endothelial cells, and fibroblasts (Springer et al., supra).

Human LFA-3 has been purified from human erythrocytes (Dustin et al., supra). It is a glycoprotein of 60,000 to 70,000 molecular weight, having a sugar content of about 50%. This purified LFA-3 binds to CD2 on the surface of T-lymphocytes and inhibits adhesion between T-lymphocytes and erythrocytes (Dustin et al., supra).

However, for ultimate use in therapy and diagnosis larger amounts of less costly LFA-3 are required than would be available from purification from erythrocytes. Moreover, for therapeutic use it would be more preferable to obtain LFA-3 from a source other than human erythrocytes, which may be contaminated with viruses, such as hepatitis B viruses or AIDS viruses.

SUMMARY OF THE INVENTION

This invention solves these problems. It provides in large amounts LFA-3 and derivatives that bind to CD2, the receptor on the surface of T-lymphocytes. More preferably, the LFA-3 of this invention and its derivatives bind to CD2 on the surface of T-lymphocytes. Most preferably, they also inhibit adhesion between T-lymphocytes and target cells. It also provides LFA-3 essentially free of other proteins of human origin and in a form that is not contaminated by viruses, such as AIDS or hepatitis B.

This invention accomplishes these goals by providing DNA sequences coding on expression in an appropriate unicellular host for LFA-3 or those derivatives thereof.

This invention also provides recombinant DNA molecules containing those DNA sequences and unicellular hosts transformed with them. Those hosts permit the production of large quantities of the novel LFA-3 and derivatives of this invention for use in a wide variety of therapeutic and diagnostic compositions and methods.

The DNA sequences of this invention are selected from the group consisting of:

(a) the DNA sequence: the DNA insert carried in phage λHT16;

(b) DNA sequences which hybridize under conditions equivalent to about 20° to 27° C. below Tm to the aforementioned DNA sequence and that code on expression for polypeptides that bind to CD2, the receptor on the surface of T-lymphocytes; and (c) DNA sequences which code on expression for a polypeptide coded for on expression by any of the foregoing DNA sequences.

BRIEF DESCRIPTION OF THE DRAWINGS

FIG. 3 (which is composed of FIG. 3A and FIG. 3B) depicts the DNA sequence of the DNA insert carried in phage λHT16. FIG. 3 also depicts the nucleotide sequence of a cDNA sequence coding on expression for human LFA-3 and the amino acid sequence deduced therefrom.

DETAILED DESCRIPTION OF THE INVENTION

We isolated the DNA sequences of this invention from two libraries: a λgt10 cDNA library derived from peripheral blood lymphocytes from leukophoresis #9 and a λgt10 cDNA library derived from human tonsil. However, we could also have employed libraries prepared from other cells that express LFA-3. These include, for example, monocytes, granulocytes, CTL's, B-lymphoblastoid cells, smooth muscle cells, vascular endothelial cells and fibroblasts. We also could have used a human genomic bank.

Figure 1:
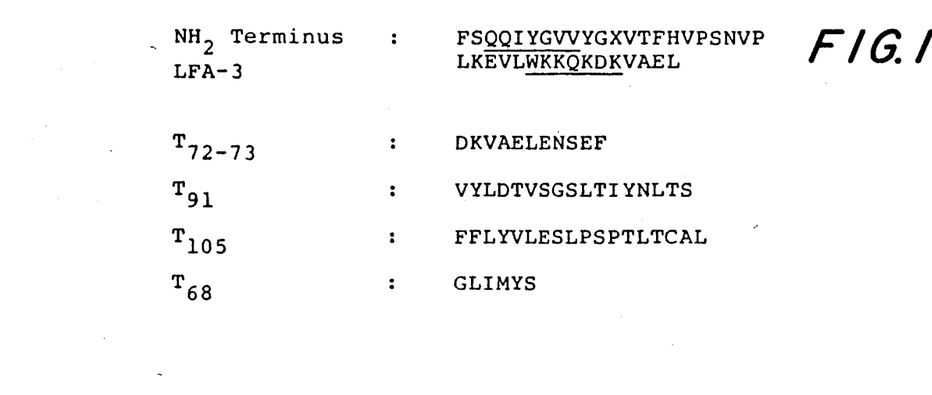
FIG. 1 depicts the amino acid sequences of the N-terminal and various peptide fragments of human LFA-3, purified from human erythrocytes using immunoaffinity chromatography.

For screening these libraries, we used a series of chemically synthesized anti-sense oligonucleotide DNA probes. We selected these probes from a consideration of the amino acid sequences of various fragments of LFA-3 that we determined using LFA-3 purified from human erythrocytes. These fragments are depicted in FIG. 1. We selected amino acids from various areas of LFA-3 that permitted the construction of oligonucleotide probes of minimal degeneracy.

Figure 2:
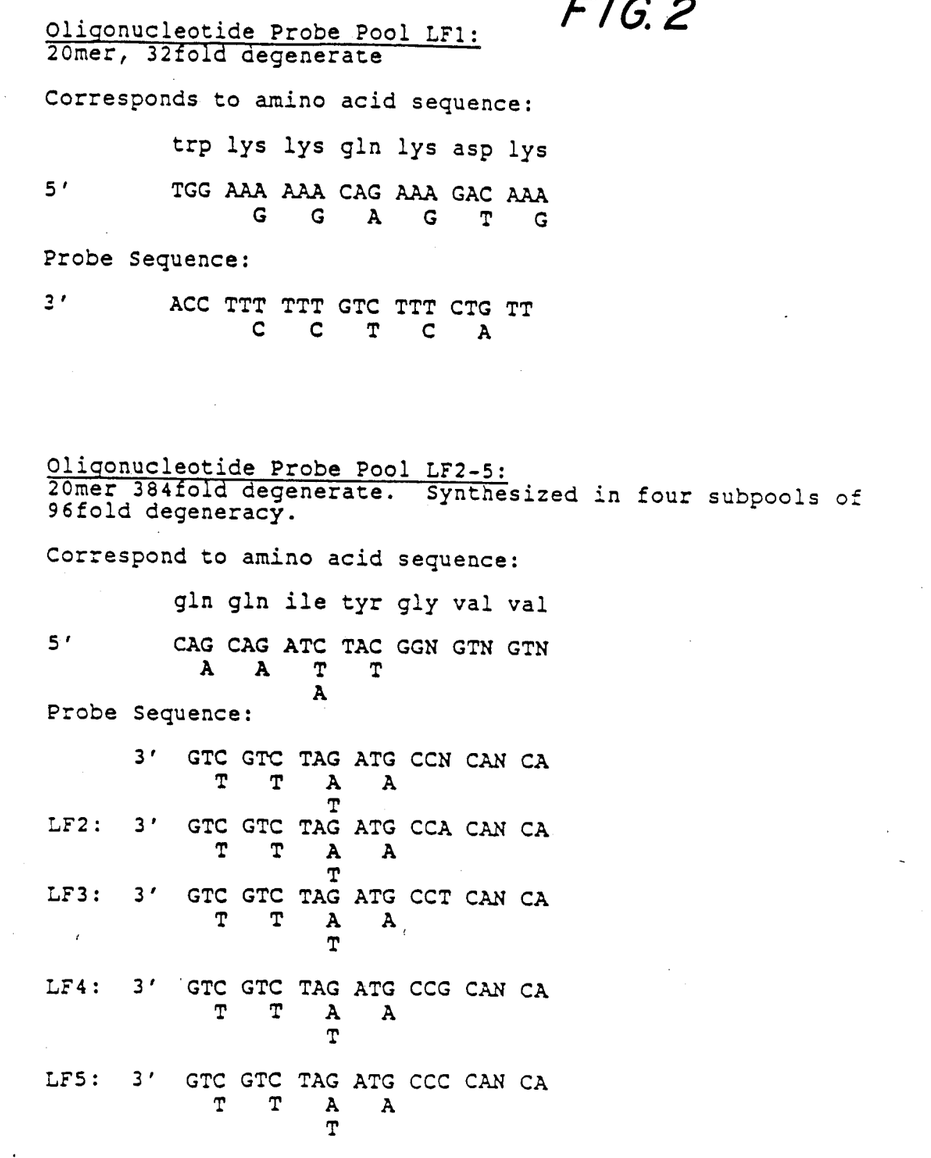
FIG. 2 depicts two pools of chemically synthesized oligonucleotide DNA probes derived from the amino acid sequence of human LFA-3 purified from human erythrocytes.

We prepared two pools of probes: LF1 and LF2-5. These pools are depicted in FIG. 2. LF1 is a 32-fold degenerate 20-mer and LF2-5 is a 384-fold degenerate 20-mer. Because of the high degeneracy of this latter pool, we subdivided the pool into four subpools—LF2, LF3, LF4 and LF5—of 96-fold degeneracy each.

For screening, we hybridized our oligonucleotide probes to our cDNA libraries utilizing a plaque hybridization screening assay. We selected clones hybridizing to several of our probes. And, after isolating and subcloning the cDNA inserts of the selected clones into plasmids, we determined their nucleotide sequences and compared the amino acid sequences deduced from those nucleotide sequences to the amino acid sequences that we had determined previously from our purified human LFA-3. As a result of these comparisons, we determined that all of our selected clones were characterized by cDNA inserts coding for amino acid sequences of human LFA-3.

We have depicted in FIG. 3 the nucleotide sequence of the longest of these cDNA inserts (the DNA insert of phage λHT16) and the DNA sequence coding for LFA-3 and the amino acid sequence deduced therefrom. As shown in FIG. 3, this cDNA insert has an open reading frame of 750 bp (250 amino acids), a 16 bp 5' untranslated region and a 201 bp 3' untranslated region. A comparison of the deduced amino acid sequence of FIG. 3 with the N-terminal amino acid sequence that we determined from LFA-3 purified from human erythrocytes suggests that amino acids -28 to -1 comprise a signal sequence and that amino acids 1 to 222 comprise the protein sequence of mature LFA-3.

The cDNA sequence depicted in FIG. 3 and contained in deposited clone λHT16 may be used in a variety of ways in accordance with this invention. It, portions of it, or synthetic or semi-synthetic copies of them, may be used as DNA probes to screen other human or animal cDNA or genomic libraries to select by hybridization other DNA sequences that are related to LFA-3.

Typically, conventional hybridization conditions, e.g., about 20° to 27° C. below Tm are employed in such selections. However, less stringent conditions may be necessary when the library is being screened with a probe from a different species than the library, e.g., the screening of a mouse library with a human probe.

The cDNA sequence of FIG. 3, portions of it, or synthetic or semi-synthetic copies of them, may also be used as starting materials to prepare various mutations. Such mutations may be either degenerate, i.e., the mutation does not change the amino acid sequence encoded for by the mutated codon, or non-degenerate, i.e., the mutation changes the amino acid sequence encoded for by the mutated codon. Both types of mutations may be advantageous in producing or using LFA-3's of this invention. For example, these mutations may permit higher levels of production, easier purification or higher LFA-3 activity.

For all of these reasons, the DNA sequences of this invention are selected from the group consisting of:

(a) the DNA sequence: the DNA insert carried in phage λHT16;

(b) DNA sequences which hybridize under conditions equivalent to about 20° to 27° C. below Tm to the aforementioned DNA sequence and which code on expression for a polypeptide that binds to CD2, the receptor on the surface of T-lymphocytes; and (c) DNA sequences which code on expression for a polypeptide coded for on expression by any of the foregoing DNA sequences.

Preferably, the DNA sequences of this invention code for a polypeptide having the sequence depicted for amino acids 1 to 222 of FIG. 3 (with or without an additional N-terminal methionine) or portions thereof. More preferably, the DNA sequence for this invention will be modified as compared to that of FIG. 3 (amino acids 1 to 222) in order to remove from it those portions that code for the hydrophobic transmembrane portion, e.g., from about nucleotide 662 to 715, to allow production of a smaller protein. Most preferably, the DNA sequences of this invention code for soluble proteins or peptides that bind to CD2, the receptor on the surface of T-lymphocytes. More preferably, the LFA-3 and derivatives of this invention bind to CD2 on the surface of T-lymphocytes. Most preferably, they also inhibit adhesion between T-lymphocytes and target cells.

The DNA sequences of this invention are also useful for producing the LFA-3 or its derivatives coded on expression by them in unicellular hosts transformed with those DNA sequences. As well known in the art, for expression of the DNA sequences of this invention the DNA sequence should be operatively linked to an expression control sequence in an appropriate expression vector and employed in that expression vector to transform an appropriate unicellular host.

Such operative linking of a DNA sequence of this invention to an expression control sequence, of course, includes the provision of a translation start signal in the correct reading frame upstream of the DNA sequence. If the particular DNA sequence of this invention being expressed does not begin with a methionine, e.g., mature LFA-3 which begins with a phenylalanine, the start signal will result in an additional amino acid—methionine—being located at the N-terminus of the product. While such methionyl-containing-product may be employed directly in the compositions and methods of this invention, it is usually more desirable to remove the methionine before use. Methods are available in the art to remove such N-terminal methionines from polypeptides expressed with them. For example, certain hosts and fermentation conditions permit removal of substantially all of the N-terminal methionine in vivo. Other hosts require in vitro removal of the N-terminal methionine. However, such in vivo and in vitro methods are well known in the art.

A wide variety of host/expression vector combinations may be employed in expressing the DNA sequences of this invention. Useful expression vectors, for example, may consist of segments of chromosomal, non-chromosomal and synthetic DNA sequences, such as various known derivatives of SV40 and known bacterial plasmids, e.g., plasmids from *E.coli* including col E1, pCR1, pBR322, pMB9 and their derivatives, wider host range plasmids, e.g., RP4, phage DNAs, e.g., The numerous derivatives of phage λ, e.g., NM989, and other DNA phages, e.g., M13 and *Filamenteous* single stranded DNA phages, yeast plasmids such as the 2μ plasmid or derivatives thereof, and vectors derived from combinations of plasmids and phage DNAs, such as plasmids which have been modified to employ phage DNA or other expression control sequences. For animal Cell expression, we prefer to use plasmid BG312, a plasmid containing the major late promoter of adenovirus 2.

In addition, any of a wide variety of expression control sequences—sequences that control the expression of a DNA sequence when operatively linked to it—may be used in these vectors to express the DNA sequence of this invention. Such useful expression control sequences, include, for example, the early and late promoters of SV40 or the adenovirus, the lac system, the trp system, the TAC or TRC system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells or their viruses, and various combinations thereof. For animal cell expression, we prefer to use an expression Control sequence derived from the major late promoter of adenovirus 2.

A wide variety of unicellular host cells are also useful in expressing the DNA sequences of this invention. These hosts may include well known eukaryotic and prokaryotic hosts, such as strains of *E. coli*, Pseudomonas, Bacillus, Streptomyces, fungi, such as yeasts, and animal cells, such as CHO and mouse cells, African green monkey cells, such as COS1, COS7, BSC1, BSC40, and BMT10, and human cells and plant cells in tissue culture. For animal cell expression, we prefer mouse L-cells.

It should of course be understood that not all vectors and expression control sequences will function equally well to express the DNA sequences of this invention. Neither will all hosts function equally well with the same expression system. However, one of skill in the art may make a selection among these vectors, expression control sequences, and hosts without undue experimentation and without departing from the scope of this invention. For example, in selecting a vector, the host must be considered because the vector must replicate in it. The vector's copy number, The ability to control that copy number, and the expression of any other proteins encoded by the vector, such as antibiotic markers, should also be considered.

In selecting an expression control sequence, a variety of factors should also be considered. These include, for example, the relative strength of the system, its controllability, and its compatibility with the particular DNA sequence, of this invention, particularly as regards potential secondary structures. Unicellular hosts should be selected by consideration of their compatibility with the chosen vector, the toxicity of the product coded on expression by the DNA sequences of this invention to them, their secretion characteristics, their ability to fold proteins correctly, Their fermentation requirements, and the ease of purification of the products coded on expression by the DNA sequences of this invention.

Within these parameters one of skill in the art may select various vector/expression control system/host combinations that will express the DNA sequences of this invention on fermentation or in large scale animal culture, e.g., mouse L cells.

The polypeptides produced on expression of the DNA sequences of this invention may be isolated from the fermentation or animal cell cultures and purified in a variety of ways well known in the art. Such isolation and purification techniques depend on a variety of factors, such as how the product is produced, whether or not it is soluble or insoluble, and whether or not it is secreted from the cell or must be isolated by breaking the cell. One of skill in the art, however, may select the most appropriate isolation and purification techniques without departing from the scope of this invention.

The polypeptides produced on expression of the DNA sequences of this invention, e.g., met-LFA-3 (amino acids 1–222 of FIG. 3) or LFA-3 (amino acids 1–222 of FIG. 3), the preferred smaller less hydrophobic derivatives thereof, or the more preferred soluble derivatives thereof, are essentially free of other proteins of human origin and are not contaminated by viruses, such as hepatitis B virus and AIDS. Thus, they are different than LFA-3 purified from human erythrocytes.

These polypeptides are useful in compositions and methods to block or to augment the immune response. For example, the polypeptides of this invention are active in inhibiting cytolytic T-lymphocyte activity by interfering with their interaction with target cells. They have a similar effect on the immune response because they interfere with the interaction of helper T-cells and antigen-presenting cells. Furthermore, the compounds of this invention may be used to target specific T cells for lysis and immune suppression or to deliver drugs, such as lymphokines, to the specifically targeted T-cells. More preferably, soluble derivatives of the polypeptides of this invention may be employed to saturate the CD2 sites of T-lymphocytes thus inhibiting T-cell activation. This effect is plainly of great utility in graft-vs-host disease, in autoimmune diseases, e.g., rheumatoid arthritis, and in preventing allograft rejection. Furthermore, the polypeptides of this invention are preferred over monoclonal antibodies to LFA-3 or CD2 because the polypeptides of this invention are less likely to elicit immune responses in humans than are antibodies raised in species other than humans. The therapeutic compositions of this invention typically comprise an immunosuppressant or enhancement effective amount of such polypeptide and a pharmaceutically acceptable carrier. The therapeutic methods of this invention comprise the steps of treating patients in a pharmaceutically acceptable manner with those compositions.

The compositions of this invention for use in these therapies may be in a variety of forms. These include, for example, solid, semi-solid and liquid dosage forms, such as tablets, pills, powders, liquid solutions or suspensions, liposomes, suppositories, injectable and infusable solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

Generally, the pharmaceutical compositions of the present invention may be formulated and administered using methods and compositions similar to those used for other pharmaceutically important polypeptides (e.g., alpha-interferon). Thus, the polypeptides may be stored in lyophilized form, reconstituted with sterile water just prior to administration, and administered by the usual routes of administration such as parenteral, subcutaneous, intravenous or intralesional routes.

The polypeptides of this invention or antibodies against them are also useful in diagnostic compositions and methods to detect T-cell subsets or CD2+ cells or to monitor the course of diseases characterized by excess or depleted T-cells, such as autoimmune diseases, graft versus host diseases and allograft rejection.

Finally, the polypeptides of this invention or antibodies against them are useful in separating B and T cells. For example, when bound to a solid support the polypeptides of this invention or antibodies to them will separate B and T cells.

In order that this invention may be better understood, the following examples are set forth. These examples are for purposes of illustration only, and are not to be construed as limiting the scope of the invention in any manner.

EXAMPLES

Purification and Sequencing of Human LFA-3

We purified the human LFA-3 that we employed to generate tryptic fragments and to determine the partial amino acid sequences depicted in FIG. 1 from outdated human erythrocytes (obtained from American Red Cross, Needham, Massachusetts) using a modification to procedure of Dustin et al., supra. For completeness that modified purification procedure is described below.

We purified monoclonal antibody (MAb) TS2/9 (Sanchez-Madrid et al., supra) from hybridoma culture supernatants by $(NH_4)_2SO_4$ precipitation and protein A affinity chromatography. We then used this purified MAb to prepare affinity columns for use in the following purification.

We coupled purified MAb to Sepharose CL-4B by a modification of the method of Cuatrecasas (March et al., *Anal. Biochem.*, 60, p. 149 (1974)). We activated washed Sepharose CL-4B (Pharmacia, Upsala, Sweden) with 40 mg/ml CNBr in 1 M $Na_2CO_3$ for 10 min on ice and then washed it with distilled water and 0.1 mM HCl. We filtered the activated Sepharose to a moist cake and added it to the purified antibody solution with 2-4 mg/ml IgG (LFA-3 MAb or mouse IgG) in 0.05 M NaCl and 0.1 M $NaHCO_3$ (pH 8.4). We then mixed the suspension end over end for 20 h and then blocked any remaining reactive groups by addition of ethanolamine to 50 mM and incubation for 1 h. We checked the supernatant for uncoupled antibody by measuring absorbance at 280 nm. Coupling was usually on the order of 90%. We then poured the MAb-coupled Sepharose into a column and washed it with one cycle of pH 11 and pH 3 buffers (see below) before use for affinity chromatography.

We purified the LFA-3 after solubilization with Triton X-100 by affinity chromatography as previously described (Dustin et al., supra). We performed all steps at 4° C.

We obtained outdated human erythrocytes from the American Red Cross (Needham, Mass.). We washed cells from 2 units of whole blood 3 times with PBS (pH 7.2). We then pelleted the packed cells to about 500 ml and added another 500 ml of PBS (pH 7.2) with 2% Triton X-100, 1 mM phenylmethylsulfonyl fluoride, 5 mM iodoacetamide and 0.2 trypsin inhibitor units/ml aprotinin to the red cell suspension while stirring. After 1 h we centrifuged the lysate at 150,000 g for 2 h. We then passed the cleared lysate over two columns in series at a flow rate of 20 ml/h: (1) a mouse IgG-Sepharose column (2 ml at 2 mg/ml) to absorb some contaminants and to filter out any particulate material, and (2) an LFA-3 MAb-Sepharose column (5-10 ml at 2 mg/ml). We washed the LFA-3 MAb-Sepharose column with 5 column volumes of 50 mM sodium phosphate (pH 7.2), 0.25 M NaCl, 0.1% Triton X-100, then 5 column volumes of 20 mM triethylamine (pH 11), 0.25 M NaCl, 0.1% Triton X-100 and again with 2 column volumes of the pH 7.2 buffer, all at a flow rate of 1 ml/min. We then eluted the remaining bound LFA-3 with 5 column volumes of 50 mM glycine HCl (pH 3), 0.25 M NaCl, 0.1% Triton X-100 at a flow rate of 20 ml/h. We neutralized the eluted LFA-3 by collecting into 0.1 volume of 1M Tris-HCl (pH 8.6), 0.1% Triton X-100.

When we used octyl-$\beta$-D-glucopyranoside (OG) (Calbiochem) to elute LFA-3, all steps were the same until after the high pH wash. At that point we washed the column with 5 volumes of phosphate buffer (pH 7.2), 0.15 M NaCl, containing 1% OG, and eluted the LFA-3 using glycine buffer (pH 3), 0.15 M NaCl, 1% OG. The elution profile was similar to that obtained with Triton X-100. We followed our LFA-3 purification in a semiquantitative manner using a "dot blot" assay (Hawkes et al., *Anal. Biochem.*, 119, p. 142 (1982) with $^{125}$-LFA-3 MAb.

To prepare the purified LFA-3 for trypsin digestion and amino acid sequencing, we deglycosylated it using N-glycosidase F, according to the supplier's instructions with minor modifications (Genzyme, Boston Mass.). We first separated the LFA-3 from the detergent by ethanol precipitation (Triton X-100) or ultrafiltration (OG). We then denatured the LFA-3 (1 nmol) by boiling with 25 $\mu$l of 0.5% SDS, 0.2 M 2-mercaptoethanol for 5 min. We next treated the denatured LFA-3 with 5 U/nmole N-glycanase in 50 mM Tris-HCl (pH 8.6) with 3% Triton X-100 and 10 mM 1,10-phenanthroline for 20 h at 37° C. in a final volume of 50 $\mu$l and precipitated the deglycosylated LFA-3 (NG-LFA-3) in ethanol (5 vol. 100% ethanol overnight at −20° C.).

We prepared highly purified N-glycanase treated LFA-3 (25 kd) by preparative SDS-PAGE and electroelution. We reduced N-glycanase-treated LFA-3 (approximately 350 pmoles) with 5mM DTT in 250 mM n-ethylmorpholine acetate, 1 mM EDTA, 0.2% SDS (pH 8.25) under argon for 5 min at 100° C., and alkylated it with 11 mM sodium iodoacetate for 30 min at 23° C. in the dark. We desalted the product (CM-NG-LFA-3) by gel filtration on Sephadex G-25 M equilibrated with 0.2% SDS, 250 mM N-ethylmorpholinoacetate (pH 8.25) and lyophilized it. We then dispersed the lyophilized LM-NG-LFA-3 in 10 ml absolute ethanol, stored at −20° C. for 7 days, and recovered the LFA-3 by centrifugation at 6000×g for 30 min at 4° C. We dissolved the pellet in 400 μl of 0.1 M $NH_4HCO_3$ and digested it with TPCK-trypsin (15% w/w) as described in Pepinsky et al., JBC, 261, p. 4239 (1986). We acidified the digest with formic acid to a final concentration of 20% formic acid and immediately fractionated the fragments by reverse phase high pressure liquid chromatography on a narrow bore $C_8$ column (Aquapore RP300, 0.21×10 cm; Brownlee Fabs). We eluted the resulting peptides with a gradient of acetonitrile (0–75%) in 0.1% trifluoroacetic acid at a flow rate of 0.3 ml/min (0.5 min fractions being collected). We monitored the column eluates at both 214 and 280 nm.

We subjected each of intact LFA-3 (300 pMoles), NG LFA-3 (50 pMoles) and tryptic fragments of CM-NG LFA-3 (5-50 pMoles) to automated Edman degradation using an Applied Biosystems 470A gas phase sequencer in the presence of polybrene (Hewick et al., JBC, 256, p. 7990 (1981)). We identified PTH-amino acids on-line using an Applied Biosystems 120A PTH analyzer. Sequencing of the intact protein yielded a sequence of 38 amino acids as shown in FIG. 1. Four tryptic fragments, $T_{72-73}$, $T_{91}$, $T_{105}$, and $T_{68}$ yielded the other DNA sequenCes, which are shown in FIG. 1.

Synthesis of Oligonucleotide Probes

We chemically synthesized two pools of anti-sense oligonucleotide DNA probes coding for regions from the amino terminal sequence of LFA-3 characterized by minimal nucleic acid degeneracy (see underscoring in FIG. 1) on an Applied Biosystems 30A DNA synthesizer. For each selected amino acid sequence, we synthesized pools of probes complementary to all possible codons. We synthesized the probes anti-sense to enable hybridization of them to the corresponding sequences in DNA as well as in mRNA. We labelled our oligonucleotide probes using [$\gamma$-$^{32}$P]-ATP and polynuceotide kinase (Maxam and Gilbert, Proc. Natl. Acad. Sci., 74, p. 560 (1977)).

As depicted in FIG. 2, the oligonucleotide probe pool LF1 was a 20-mer with 32-fold degeneracy. Probe pool LF2-5, was a 20-mer with 384-fold degeneracy. However, to reduce its degeneracy, we synthesized this pool in four subpools of 96-fold degeneracy each by spitting the degenerate codon for Gly into one of its four possible nucleotides for each subpool. We then selected the subpool containing the correct sequence from the three pools containing incorrect sequences by hybridization of the individual subpools to Northern blots containing human tonsil mRNA, as described previously (Wallner et al., Nature, 320, pp. 77–81 (1986)). Oligonucleotide probe subpool LF2 hybridized to a 1300 nucleotide transcript in human tonsil RNA, which suggested that it contained the correct sequence. Hence, we used it and pool LF1 for screening our various libraries.

Construction of λgt10 Peripheral Blood Lymphocytes cDNA Library

To prepare our Peripheral Blood Lymphocytes (PBL) DNA library, we processed PBL from leukophoresis #9 through one round of absorption to remove monocytes. We then stimulated the non-adherent cells with IFN-γ1000 U/ml and 10 μg/ml PHA for 24 h. We isolated RNA from these cells using phenol extraction (Maniatis et al., Molecular Cloning, p. 187 (Cold Spring Harbor Laboratory) (1982)) and prepared poly A+ mRNA by one round of oligo dT cellulose chromatography. We ethanol precipitated the RNA, dried it in a speed vac and resuspended the RNA in 10 μl $H_2O$ (0.5 μg/μl ). We treated the RNA for 10 min at room temperature in $CH_3HgOH$ (5mM final concentration) and β-mercaptoethanol (0.26 M). We then added the methyl mercury treated RNA to 0.1 M Tris-HCl (pH 8.3) at 43° C., 0.01 M Mg, 0.01 M DTT, 2 mM Vanadyl complex, 5 μg oligo $dT_{12-18}$, 20 mM KCl, 1 mM dCTP, dGTP, dTTP, 0.5 mM dATP, 2 μCi[α-$^{32}$P]dATP and 30 U 1.5μl AMV reverse transcriptase (Seikagaku America) in a total volume of 50 μl. We incubated the mixture for 3 min at room temperature and 3 h at 44° C. after which time we stopped the reaction by the addition of 2.5 μl of 0.5 M EDTA.

We extracted the reaction mixture with an equal volume of phenol:chloroform (1:1) and precipitated the aqueous layer two times with 0.2 volume of 10 M $NH_4AC$ and 2.5 volumes EtOH and dried it under vacuum. The yield of cDNA was 1.5 μg.

We synthesized the second strand according to the methods of Okayama and Berg (Mol. Cell. Biol., 2, p. 161 (1982)) and Gubler and Hoffman (Gene, 25, p. 263 (1983)), except that we used the DNA polymerase I large fragment in the synthesis.

We blunt ended the double-stranded cDNA by resuspending the DNA in 80 μl TA buffer (0.033 M Tris Acetate (pH 7.8); 0.066 M KAcetate; 0.01M MgAcetate; 0.001M DTT; 50 μg/ml BSA), 5 μg RNase A, 4 units RNase H, 50 μM βNAD, 8 units E.coli ligase, 0.3125 mM dATP, dCTP, dGTP, and dTTP, 12 units $T_4$ polymerase and incubated the reaction mixture for 90 min at 37° C., added 1/20 volume of 0.5M EDTA, and extracted with phenol:chloroform. We chromatographed the aqueous layer on a G150 Sephadex column in 0.01M Tris-HCl (pH 7.5), 0.1 M NaCl, 0.001 M EDTA and collected the lead peak containing the double-stranded cDNA and ethanol precipitated it. Yield: 605 μg cDNA.

We ligated the double-stranded cDNA to linker 35/36 using standard procedures. We then size selected the cDNA for 800 bp and longer fragments on a S500 Sephacryl column, and ligated it to EcoRI digested λgt10. We packaged aliquots of the ligation reaction in Gigapak (Strategene) according to the manufacturer's protocol. We used the packaged phage to infect E.coli BNN102 cells and plated the cells for amplification. The resulting library contained 1.125×10$^6$ independent recombinants.

Screening of the Libraries

We screened human tonsil λgt10 cDNA library (Wong et al., Proc. Natl. Acad. Sci., 82, p. 7711-775 (1985)) and the PBL cDNA library prepared above with our labelled oligonucleotide probe LF1 using the plaque hybridization screening technique of Benton and Davis (Science, 196, p. 180 (1977)).

We pelleted an overnight culture of BNN102 cells in L broth and 0.2% maltose and resuspended it in an equal volume of SM buffer (50 mM Tris-HCl (pH 7.5), 100 mM NaCl, 10 mM MgSO$_4$, and 0.01% gelatin). Thereafter, we preabsorbed 9 ml of cells with $1.5 \times 10^6$ phage particles at room temperature for 15 min and plated them on 30 LB Mg plates.

After incubation at 37° C. for 8 h, we lifted the filters from the plates and lysed them by placing them onto a pool of 0.5 N NaOH/1.5 M NaCl for 5 min, and then submerged them for 5 min in the same buffer. We neutralized the filters by submerging them in 5 min each, and rinsed them for 2 min in 1 M NH$_4$OAc, air dried the filters, and baked them for 2 h at 80° C.

We prehybridized and hybridized the filters to oligonucleotide probe LFl in 0.2% polyvinylpyrolidone, 0.2% ficoll (MW 400,000), 0.2% bovine serum albumin, 0.05 M Tris-HCl (pH 7.5), 1 M sodium chloride, 0.1% sodium pyrophosphate, 1% SDS, 10% dextran sulfate (MW 500,000) and 100 µg/ml tRNA. We detected the hybridizing λ-cDNA sequences by autoradiography.

We initially selected 26 positive phages from the PBL library and 12 positive phages from the tonsil library. We then rescreened these clones and plaque purified them at lower density using the same probe.

We digested isolated DNA from these clones with EcoRI and hybridized them to oligomer probes LF1 and LF2 using the Southern blot technique (E. M. Southern, *J. Mol. Biol.*, 98, pp. 503–18 (1975)). We then further characterized the DNA from two clones of the tonsil library (λHT16 and λHT12) and two clones from the PBL library (λP26 and λP24) by DNA sequencing analysis.

Sequencing of cDNA Clones

We subcloned the EcoRI digested DNA from clones λHT16 and λP26 into vector pNN01 to facilitate sequence analysis.* λHT16 has 2 EcoRI fragments which we individually subcloned into pNN01 resulting in plasmids pHT16H and pHT16L. The entire insert of λP26 is contained on a single NotI fragment. For subcloning, we used the vector's EcoRI site or SmaI site employing techniques in common use.

Figure 4:
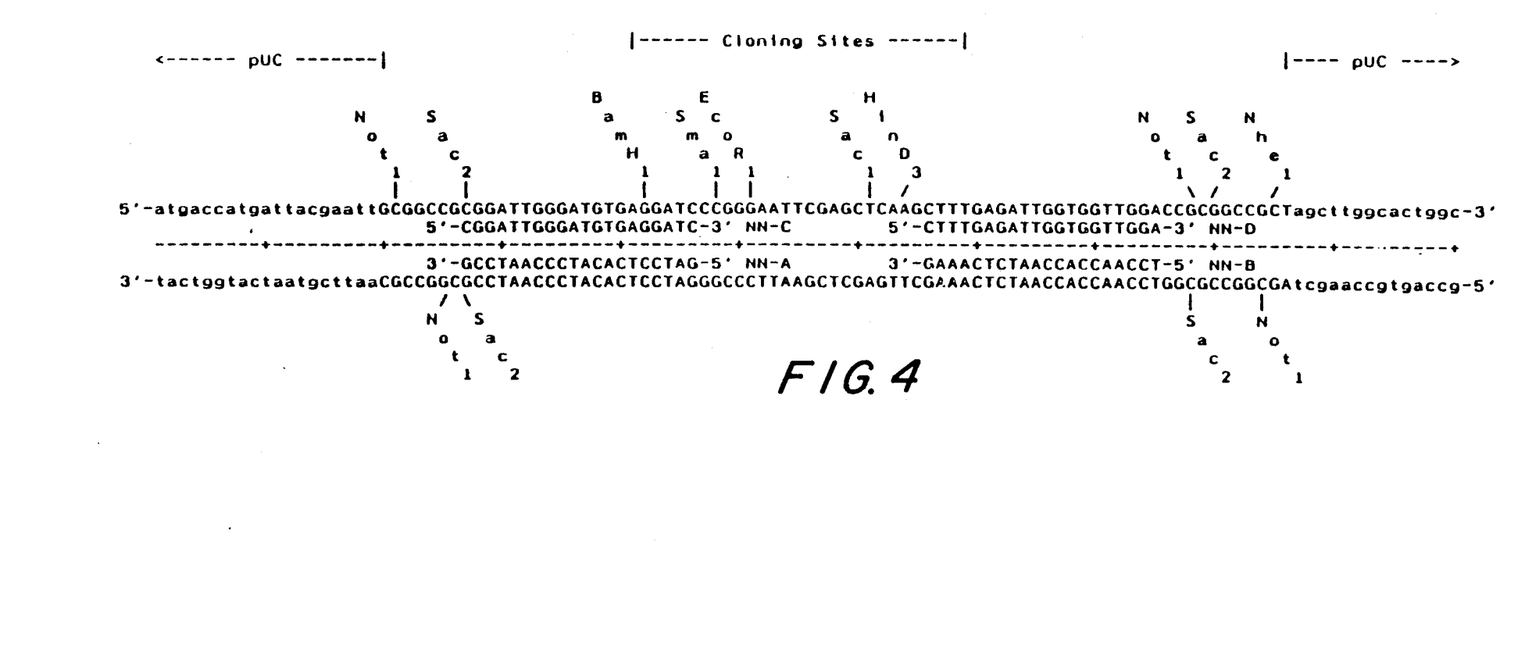
FIG. 4 depicts the relevant portions of sequencing plasmid pNN01.

*We constructed sequencing plasmid pNN01 by removing the synthetic polylinker of pUC8 by restriction digestion and replacing it with a new synthetic segment. The 2.5 kb backbone common to the pUC plasmids, which provides an origin of replication and confers ampicillin resistance, is unchanged. The novel synthetic portion of pNN01 is shown in FIG. 4.

Figure 5:
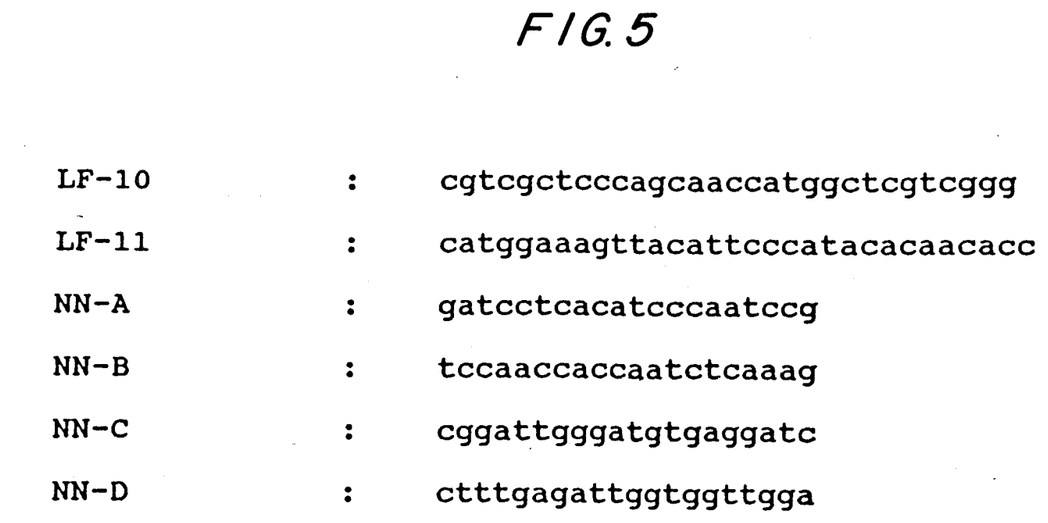
FIG. 5 depicts the nucleotide sequence of probes LF-10, LF-11, NN-A, NN-B, NN-C, and NN-D.

We determined the DNA sequences of our subclones largely by the method of Maxam and Gilbert (*Meth. Enzymology*, 1980). However, for some fragments, we used the related procedure of Church and Gilbert (*Proc. Natl. Acad. Sci. USA*, 81, p. 1991 (1984)). The structure of pNN01 enables sequencing, by the Church-Gilbert approach, of the ends of an inserted fragment using NotI digestion and four 20-nucleotide long probes: NN-A, NN-B, NN-C and NN-D. See FIG. 5.

Two sequencing results of significance were obtained directly from our subclones by the Church-Gilbert method. In one experiment, we probed PvuII digested DNA from λHT16 independently with LF10 and LF11 (FIG. 5) to determine the sequence across the EcoRI sites bounding the 224 bp EcoRI fragment. This directly refuted the possibility that the analysis of the two EcoRI subclones (pHT16H and pHT16L) of this phage had overlooked sequences either 5' to the small EcoRI fragment or between the two EcoRI fragments. We also confirmed this result by analysis of the NotI subcloned pP26, which has this EcoRI site intact. We also digested pP26 with PvuII and sequenced the fragment by the Church-Gilbert method using LF10 (FIG. 5) as hybridization probe. This proved that the 5' terminus of the insert of λP26 was exactly the same as that of λHT16.

Figure 3A:
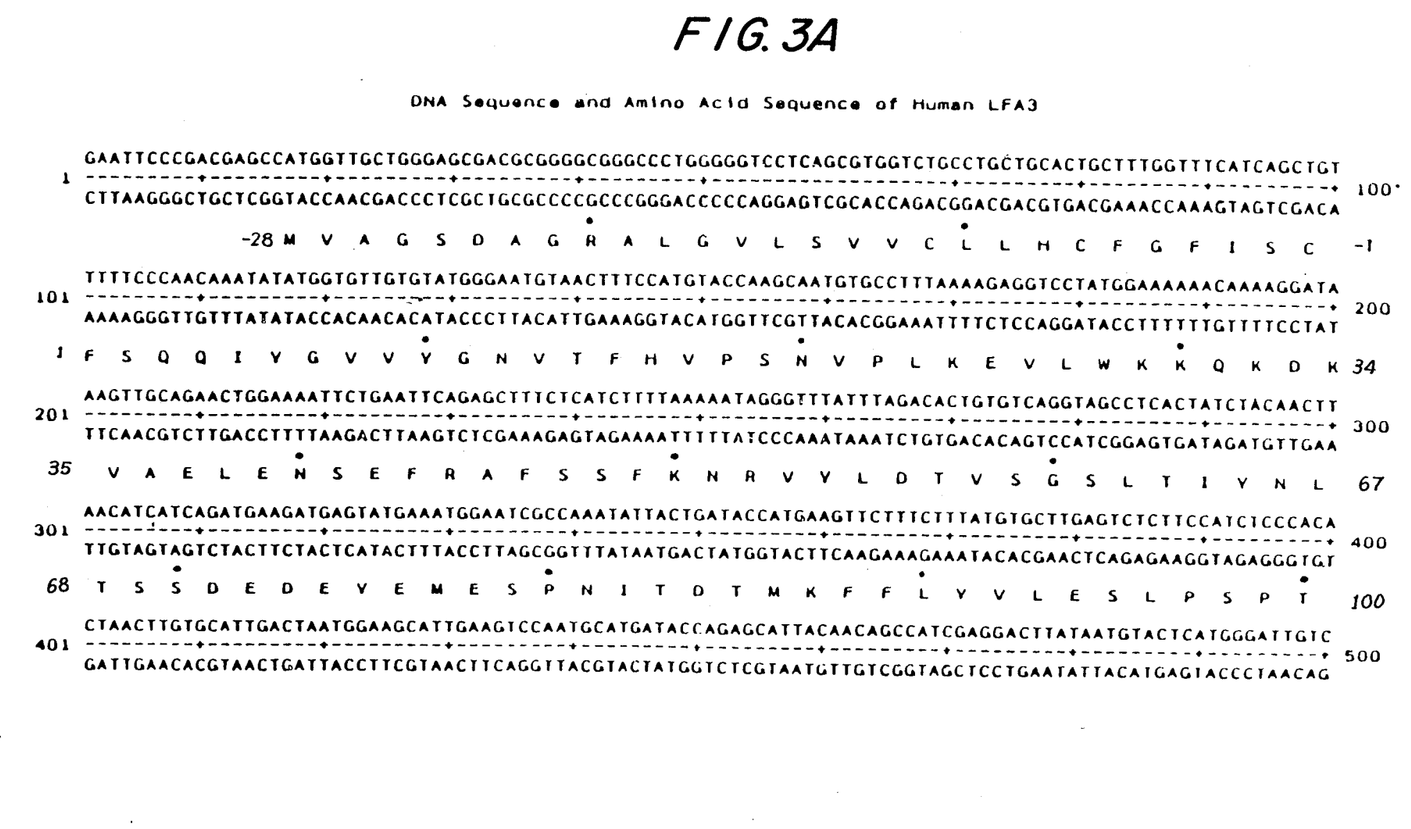
Figure 3B:
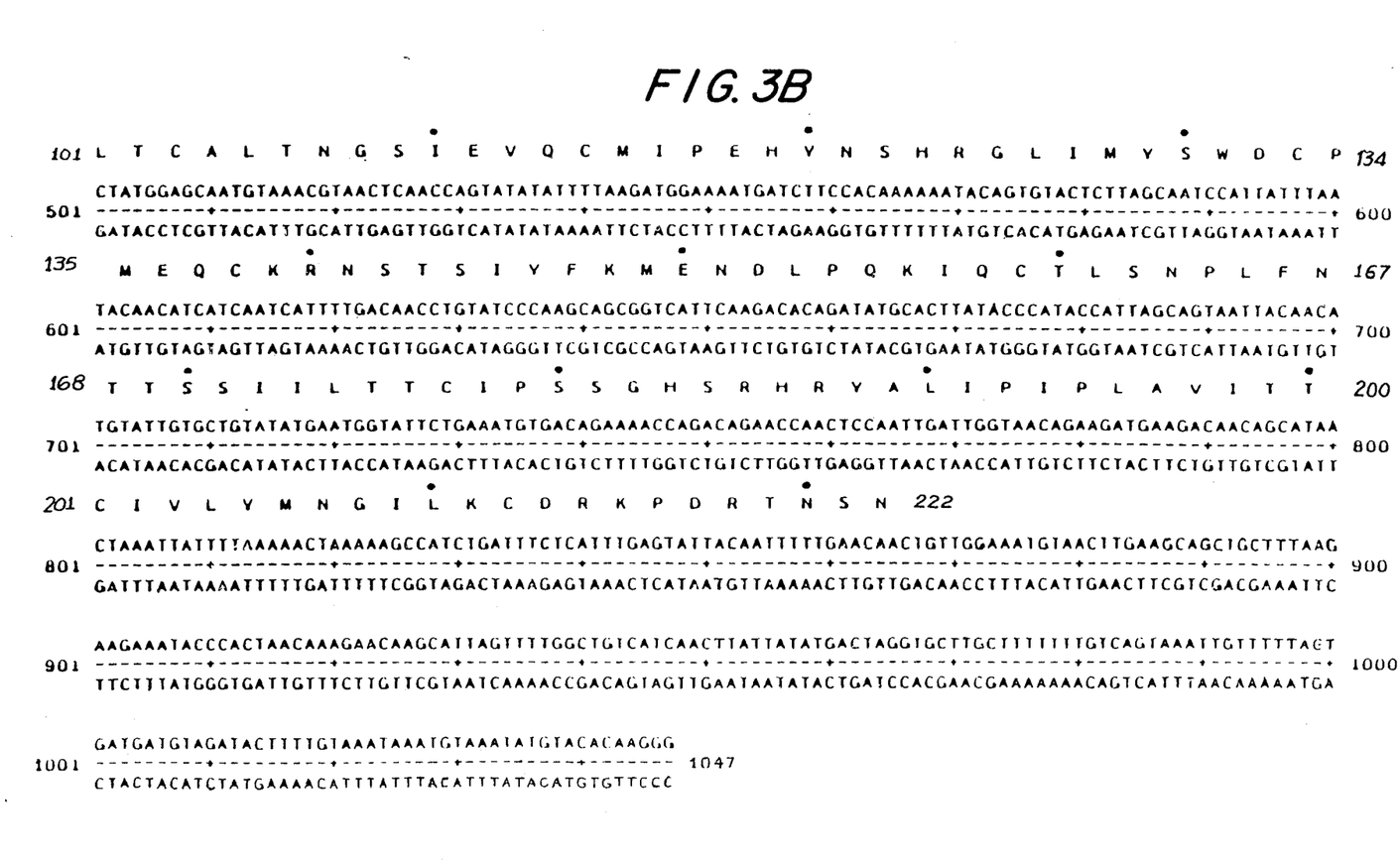

FIG. 3 i.e., FIGS. 3A and 3B taken together show the DNA sequence of the cDNA insert of phage λHT16. It also depicts the DNA sequence coding for LFA-3 and the amino acid sequence deduced therefrom. This latter cDNA, e.g., that coding for LFA-3, contained DNA sequences coding for the amino acid sequences that we had determined for the N-terminal region and the 4 tryptic fragments of LFA-3 purified from human erythrocytes.

Expression of LFA-3 in Animal Cells

To express our DNA sequence coding for LFA-3 in animal cells, the 946 bp NcoI (Klenow)/MaeI fragment of λHT16, which contains the full coding sequence and a portion of the 3' untranslated region of LFA-3, is inserted into the SmaI site of animal expression vector BG312 (Cate et al., *Cell*, 45, p. 685 (1986)). In this vector, the expression of the inserted DNA sequence is under the control of the adenovirus 2 late promoter. Mouse L-cells are then transfected with our vector BG312 (LFA-3) to obtain transient expression of the LFA-3 coding sequence of that vector.

To increase the level of expression, the 1.2 Kb BglII fragment of vector BG312(LFA-3) is inserted into expression vector BG312/PY7. This vector carries the polyoma Ta gene (*Science*, 209, p. 142 (1980); PNA, 78, p. 2072 (1981)) which allows replication of the vector in L-cells, thus, increasing the copy number of the vector and the LFA-3 DNA sequence carried by it.

For expression in stable cell lines, mouse L-cells are cotransfected with BG312/Y7(LFA-3) and pOPK (tk) (Grosveld et al., *Nucl. Acids. Res.*, 10, p. 6715 (1982)). The LFA-3 produced in these cells is purified using the procedure of Dustin et al. (supra).

For expression of our most preferred soluble LFA-3 derivatives similar expansion plasmids and hosts are used. In these cells the soluble LFA-3 is secreted into the medium and is purified using the procedure of Dustin et al. (supra).

To enable further the above-described invention, we deposited the following phage carrying an LFA-3 DNA sequence of this invention in the In Vitro International, Inc. Culture Collection in Linthioum, Maryland, on May 28, 1987:

λHT16 [λgt10/LFA-3]

The phage has been assigned accession number IVI 10133.

While we have herein before presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than the specific embodiments which we have presented by way of example.

We claim:

1. A DNA sequence selected from the group consisting of:

(a) the DNA sequence which codes for the LFA-3 polypeptide carried in phage λHT16;

(b) DNA sequences which hybridize under conditions equivalent to about 20° to 27° C. below Tm and 1 M sodium chloride to the LFA-3 DNA sequence of (a) and which code on expression for a polypeptide that binds to CD2, the receptor on the surface of T-lymphocytes; and (c) DNA sequences which code on expression for a polypeptide that binds to CD2 which is coded for on expression by any of the foregoing DNA sequences.

2. The DNA sequence according to claim 1, wherein said DNA sequence (b) codes on expression for a polypeptide that binds to CD2 on the surface of T-lymphocytes and inhibits adhesion between T-lymphocytes and target cells.

3. The DNA sequence according to claim 2, wherein said polypeptide is soluble.

4. The DNA sequence according to claim 1, wherein said DNA sequence is selected from the group consisting of a DNA sequence of the formula $N_{1-1047}$ of FIG. 3, a DNA sequence of the formula $N_{17-766}$ of FIG. 3, a DNA sequence of the formula $N_{101-766}$ of FIG. 3, a DNA sequence of the formula $N_{101-611}$–$N_{716-766}$ of FIG. 3, a DNA sequence of the formula ATG-$N_{101-766}$ of FIG. 3, a DNA sequence of the formula ATG-$N_{101-661}$-$N_{716-766}$ of FIG. 3, and DNA sequences that code on expression for any of the above DNA sequences.

5. The DNA sequence according to claim 4, wherein said DNA sequence is selected from the group consisting of a DNA sequence of the formula $N_{17-766}$ of FIG. 3, a DNA sequence of the formula ATG-$N_{17-766}$ of FIG. 3, and DNA sequences that code on expression for any of the above DNA sequences.

6. A recombinant DNA molecule comprising a DNA sequence selected from the group consisting of the DNA sequences of claims 1 to 5, said DNA sequence being operatively linked to an expression control sequence in said recombinant DNA molecule.

7. The recombinant DNA molecule according to claim 6, wherein said expression control sequence is selected from the group consisting of the early or late promoters of SV40 or adenovirus, the lac system, the trp system, the TAC system, the TRC system, the major operator and promoter regions of phage λ, the control regions of fd coat protein, the promoter for 3-phosphoglycerate kinase or other glycolytic enzymes, the promoters of acid phosphatase and the promoters of the yeast α-mating factors.

8. A unicellular host transformed with a recombinant DNA molecule selected from the group consisting of the recombinant DNA molecules of claim 6.

9. The host according to claim 8, wherein said host is selected from the group consisting of strains of *E.coli*, Pseudomonas, Bacillus, Streptomyces, fungi, animal cells, plant cells and human cells in tissue culture.

10. A method of producing a LFA-3 polypeptide comprising culturing a unicellular host transformed with a recombinant DNA molecule selected from the group consisting of the recombinant DNA molecules of claim 6 or 7.

* * * * *